United States Patent [19]
Zawadzki

[11] Patent Number: 4,844,888
[45] Date of Patent: Jul. 4, 1989

[54] POLYSILOXANE COSMETIC COMPOSITION

[75] Inventor: Mary E. Zawadzki, Cambridge, Mass.

[73] Assignee: The Gillette Company, Boston, Mass.

[21] Appl. No.: 120,549

[22] Filed: Nov. 13, 1987

[51] Int. Cl.4 .............................................. A61K 7/035
[52] U.S. Cl. ...................................... 429/69; 424/70;
424/71; 132/203; 524/511; 525/477;
106/287.11; 106/287.12; 106/287.13;
106/287.14
[58] Field of Search ........................ 424/47, 69, 70, 71,
424/DIG. 1, DIG. 2; 132/7; 524/588; 525/477;
106/287.11, 287.12, 287.13, 287.14

[56] References Cited

U.S. PATENT DOCUMENTS

| | | | |
|---|---|---|---|
| 3,595,885 | 7/1971 | Rossmy et al. | 424/70 |
| 4,240,450 | 12/1980 | Grollier et al. | 424/70 |
| 4,311,626 | 1/1982 | Ona et al. | 525/477 |
| 4,342,742 | 8/1982 | Sebey et al. | 424/71 |
| 4,409,267 | 10/1983 | Ichinohe et al. | 156/321 |
| 4,419,391 | 12/1983 | Tanaka et al. | |
| 4,490,356 | 12/1984 | Sebag et al. | 424/70 |
| 4,523,921 | 6/1985 | Sebay et al. | 9/407 |
| 4,559,385 | 12/1985 | Huhn et al. | 524/838 |
| 4,563,347 | 1/1986 | Starch | 424/70 |
| 4,586,518 | 5/1988 | Cornwall et al. | 424/70 |
| 4,601,902 | 7/1986 | Fridd et al. | 424/70 |
| 4,618,689 | 10/1986 | Traver et al. | 556/425 |
| 4,631,207 | 12/1986 | Price | 422/317 |
| 4,658,049 | 4/1987 | Nakano et al. | 556/437 |

FOREIGN PATENT DOCUMENTS 0095238 11/1983 European Pat. Off. .

Primary Examiner—Ellis P. Robinson
Assistant Examiner—P. J. Ryan

[57] ABSTRACT

A hair-treating and skin-treating composition comprising a liquid preferably aqueous dispersion containing a mixture of two type of polysiloxanes, one being amino- and hydroxy- or alkoxy-functional, the other being carboxy- or carboxyl-ester-functional containing at least two carboxyl groups, the composition being characterized by ready removability from hair and skin after drying by washing.

13 Claims, No Drawings

POLYSILOXANE COSMETIC COMPOSITION

This invention relates to a composition comprising a novel liquid dispersion containing a combination of two types of siloxane polymers and a method of making the same. The composition is useful either alone or in combination with additional components as a cosmetic composition for treating hair or for application to skin.

There have previously been proposed in U.S. Pat. Nos. 4,409,267, 4,419,391, and 4,631,207, a variety of amino-functional polysiloxanes for treating fabrics or fibers or for waterproofing masonry. In Huhn et al. U.S. Pat. No. 4,559,385, there were described complex mixtures of hydroxy-functional polysiloxanes, amino-functional polysiloxanes, organo silanes, and a condensation catalyst for treating a variety of natural and synthetic fibers. Hair treating compositions containing amino functional polysiloxanes have been described in Cornwall et al. U.S. Pat. No. 4,586,518, Fridd et al, U.S. Pat. No. 4,601,902, and Traver et al. U.S. Pat. No. 4,618,689. in Sebag et al. U.S. Pat. No. 4,342,742 and Sebag et al. U.S. Pat. No. 4,490,536, there were described polysiloxane products having ay one of a variety of hydrophilic groups including amino-functional and carboxy-functional groups bonded to the silicon atoms by a decamethylene chain. The products were said to be useful in a variety of hair treating compositions including shampoos, dyes, setting lotions and waving compositions.

In Japanese Pat. No. 58605 (1982) there was described a composition containing an amino functional polysiloxane along with a dibasic carboxylic acid or an amino acid for use in cosmetics applied to hair and skin. In Japanese Pat. No. 144179 (1983) there was described a process for treating cloth to make it durably water repellent by applying to it in sequence an amino functional polyalkoxysilane, followed by carboxy- or carboxy ester-functional polysiloxane. Ona et al. U.S. Pat. No. 4,311,626 described a composition for treating natural or synthetic fibers and fabrics to impart a combination of properties durable to washing and dry cleaning; the composition contained an amino fjunctional polysiloxane free from alkoxy and hydroxy groups, and a carboxy functional polysiloxane. Nakano et al. U.S. Pat. No. 4,658,049 described a carboxy-functional polysiloxane having a variety of uses, and published European Patent Application No. 0095238 described the application to hair of a composition comprising (1) a polysiloxane containing a functional group that provides attachment to the hair, (2) a surfactant (3) a freeze-thaw stablizer and (4) water. Grollier et al. U.S. Pat. No. 4,240,450 described compositions for treating hair or skin comprising a combination of a cationic polymer with an anionic polymer, the polymers being conventional carbon-type polymers free from silicon or siloxane groups.

It has now been found that a composition comprising a liquid, preferably aqueous, dispersion of two different types of polysiloxanes possesses unique advantages for treating fibers and particularly for treating hair or skin, as in a cosmetic composition. The composition when applied to hair or skin solidifies or "dries" rapidly within a few minutes after application at a temperature of 20°-30° C. and is then characterized by the fact that it can be essentially completely removed by washing with an aqueous solution of surface active agent, such as a shampoo or soap solution. Despite this ready removability, however, the dried film of the composition surprisingly remains highly resistant to moisture and to removal by water alone, and serves to retain the curl and set of the hair for an extended period even when exposed to conditions of high humidity and subjected to repeated combing; when applied to skin it serves to retain moisture. Other agents conventionally present in hair or skin treating compositions may optionally be added to provide a hair conditioner, insect repellent lotion or cream, sunscreen, or skin moisturizer, for example. The dispersion, with or without optional additives, when applied to hair, provides not only set retention but also high sheen, desirable tactile properties, and ease of combing, thus serving as a set holding cream rinse.

The composition of the present invention includes as one of the two types of polysiloxanes, a carboxy- or carboxyl- ester-functional polysiloxane (type I) having the following composition:

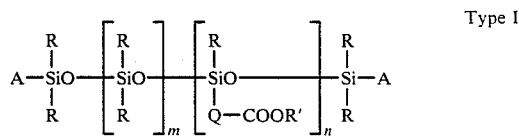

in which
R is a monovalent hydrocarbon group having 1 to 20 carbon atoms, preferably an alkyl or benzyl group having 1 to 7 carbon atoms,
R' is hydrogen or a monovalent hydrocarbon group such as an alkyl group, preferably hydrogen.
Q is a divalent hydrocarbon group having 1 to 8 carbon atoms, preferably an alkylene group having 1 to 4 carbon atoms.
A is either —R or —Q—COOR',
m and n are positive integers, the sum of m and n being from 10 to 300, and
in which at least two —COOH groups are present.

The second of the two types of polysiloxanes is an amino functional polysiloxane which includes one or more hydroxy or alkoxy groups directed to silicon (Type II) and having the following composition:

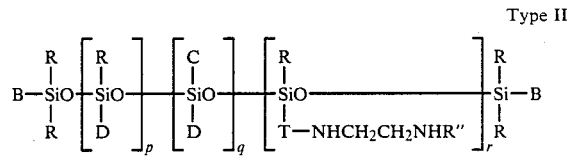

in which
R is a monovalent hydrocarbon group having 1 to 20 carbon atoms, preferably an alkyl group having 1 to 7 carbon atoms.
R" is hydrogen or R,
B is —R or —OH or —OR or —TNHCH$_2$CH$_2$NHR",
C is —OH or —OR,
D is —R, —OH or —OR,
T is a divalent hydrocarbon group having 1 to 8 carbon atoms, preferably an alkylene group having 1 to 4 carbon atoms,
p, q and r are positive integers, the sum of p, q and r being from 10 to 300, and r is at least 2, and
in which preferably at least two primary amino groups are present.

The molar ratio of Type I to Type II polysiloxane in the composition is from 1:4 to 9:1. In the case of compositions to be applied to hair, the molar ratio of Type I to Type II is preferably from 1:4 to 1:1; while in the case of composition to be applied to the skin the molar ratio is preferably from 1.5:1 to 5:1.

Polymers of the foregoing Type I are available commercially in the form of Q2-7119 (Dow Corning) and Y-7533 (Union Carbide) and can be made by conventional procedures.

Polymers of Type II are also commercially available, such as 478, 531, and Softener CSF, all from Dow Corning; and 1705 from General Electric as well as SWS-756.

The polysiloxanes employed in the present invention are essentially insoluble in water. Dispersing the Type I and Type II polysiloxanes separately in water or an aqueous medium, or dispersing a mixture of the two types in water or an aqueous medium produces a composition which, after drying on hair or skin, cannot be removed by washing with surface-active agent solution, and thus lacks an essential characteristic of the present invention.

The aqueous dispersions of the present invention are prepared by first dissolving the Type I and Type II polysiloxanes in the desired proportions in a volatile organic solvent, preferably one having a boiling point below that of water, then dispersing the solvent solution in water or aqueous medium. Although applicants do not which to be bound to any particular theory of the mode of operation or functioning of the composition, it is believed that the hydroxy or alkoxy groups of the Type II polymer condense with each other and that a chemical reaction occurs between the carboxyl groups of the Type I polysiloxane and the primary amine groups of the Type II polysiloxane resulting in partial covalent cross-linking of the two types in the dispersion before application to the hair or skin, followed by further cross-linking upon formation of a film or coating, thus producing a unique combination of advantageous properties in the film or coating.

The dispersions are prepared by first dissolving the Type I and Type II polysiloxanes in the desired proportions in a volatile organic solvent, as pointed out above. Among suitable solvents are ethers such as diethyl ether, di-n-propyl ether, and diisopropyl ether; small hydrocarbons such as pentane, hexane and benzene; alcohols such as methyl alcohol, ethyl alcohol and isopropyl alcohol; ketones such as acetone, methyl ethyl ketone and the like. The amount of solvent used is not critical; however, it is desired that the solution be sufficiently dilute so as to slow the cross-linking reaction between the two types of silicones while in solution; in general, the weight of solvent required to dissolve tbhe polysiloxanes is at least as great as the weight of the two polysiloxanes, but more solvent can be used if desired. It is undesirable to use a large excess of solvent because of the cost and difficulty of removing it during formation of the desired dispersion.

To the solution of polysiloxanes in an organic solvent may be added any desired filler, thickener, plasticizer, perfume, sunscreening or insect repellent agent, conditioner, medicament, moisturizer, wetting agent or soap, or other active agent for treating hair or skin.

To convert the solution in organic solvent to a dispersion, it is mixed with water or with an aqueous solution containing additional optional desired components or active agents, then subjected to severe mechanical mixing or shearing stress, for example in a Waring Blender or by sonication. It is also desirable to include the solution in order to facilitate formation of the dispersion a surfactant or surface active agent as a dispersing aid and stabilizer. Suitable surfactants include cationic, anionic or amphoteric surface active agents, the non-ionic surface active agents being preferred. Suitable agents include among others sodium lauryl sulfate, sodium dodecyl sulfate, polyoxyethylene (23) lauryl ether, polyoxyethylene stearate, and the like. The amount of surface active agent employed may vary depending upon the particular polysiloxane and particular surface active agent used as well as on the particle size of the dispersion, and can readily be determined in any particular case by simple tests as is well known to those skilled in the art of preparing aqueous dispersion generally. The surface active agent may be dissolved in the organic solvent solution or it may be dissolved or dispersed in water, after which the solvent solution and water are thoroughly mixed by mechanical or sonication devices to form an aqueous dispersion and the organic solvent is thereupon removed by evaporation. In order to hasten the removal of solvent, the dispersion may be subjected to reduced pressure and/or heated to its boiling point. Heating tends to accelerate the chemical cross-linking reaction believed to occur between Type I and Type II polysiloxanes.

The relative proportion of total polysiloxane to water or other liquid in the dispersion may vary over a range from about 0.25% to about 30% by weight; for best results the concentration of total polysiloxanes in the dispersion should be from about 1.5% to about 15% by weight. In the case of a composition to be applied to hair, the total polysiloxanes preferably amount to 1.5 to 5% by weight. The amount of dispersion applied to the hair may vary widely depending upon individual preferences, the manner of application, whether by spray or as a lotion or cream rinse or mousse, and the concentration of the polysiloxanes in the dispersion. If desired, the dispersion may be packaged with a conventional pressure propellent to enable it to be applied as a spray or aerosol.

When the composition of the present invention is applied to the hair and allowed to remain for as short a time as one minute, it forms a film adherent to the hair fibers which is not removed by rinsing in water. Heavier and more complete films are formed and deposited on the hair fibers if the composition is allowed to remain on the hair for a longer time before rinsing or if it is heated. Although a water rinse is frequently desired by the user, it is not essential and the composition if applied sparingly may simply be allowed to dry on the hair either at room temperature or at higher temperatures.

The film formed by the composition, with or without a water rinse, supplies desirable characteristics to the hair including a high sheen, good tactile properties and ease of combing even when wet, in addition to set retention when the hair is exposed either to dry conditions or to an atmosphere of high humidity and to repeated combing.

When applied to the skin, the compositions of the present invention "dry" i.e. solidify within as short a time as a minute or less to form an elastic water repellent film or coating which is adherent to the skin and effective in decreasing transepidermal water loss in addition to providing those special properties supplied by optional added active agents, as in the case of sunscreens, moisturizers, water proof insect repellants, medicating and protecting coatings, etc.

The compositions of this invention may be heated at room temperature to above 100° C. for several minutes to several hours without phase separation; nor does separation occur during subsequent cooling to room temperature. Such heating, particularly at temperatures above room temperature, produces a composition which forms a desirably thicker and more elastic film when applied to skin than does the composition without such heating.

The composition of the present invention is further distinguished from those of the prior art in its rapid drying or solidyfing time, high durability in conditions of high humidity or when subjected to water rinse or combing, and remarkable ease of removal by conventional shampooing or washing with soap or other effective surface active agents. In the case of hair treated with the composition of this invention, the shampoo preferably contains a small amount of a lower alkyl alcohol or benzyl alcohol, or of a low molecular weight polyalcohol such as ethylene glycol.

The following specific examples are intended to illustrate more fully the nature of the invention without acting as a limitation upon its scope.

EXAMPLE 1

A hair styling and conditioning composition designed to be applied like a cream rinse was prepared as follows:

3.5 g of Down Corning 478 Fluid (a mixture of 50% amino-methoxy-functional dimethylsilicone polymers and 50% isopropanol) and 1.5 g of Down Corning Q2-7119 Fluid (carboxylic acid-functional dimethylsilicone polymers) were mixed with 20 ml diethylether. The mixture of silicones and ether was mixed with a solution of 0.5 g Myrj 53 (PEG 50 stearate) in 44.5 g distilled water and subjected to high-shear mixing until a stable white emulsion or dispersion was produced. The ether and isopropanol was then removed from this emulsion under reduced pressure on a rotary evaporator. This emulsion was then combined with a mixture of 1.5 g Squat 95 (a stearalkonium chloride), 1.0 g Brij 52 (Polyoxyethylene(2))cetylether) and 47.5 g distilled water, which produced a white, creamy, viscous fluid.

The following test demonstrated the humidity-resistant styling properties of the foregoing composition versus the properties of a creme rinse (Tame), a styling mousse (Mink Difference Mousse Regular), a liquid styling aid (Mink Difference Liquid Stylizer) and a hair spray (Adorn Extra Hold) all of which are commercially available products. Five-inch long, 1 g tresses of dark brown, virgin hair were employed with three tresses per product. Each tress was shampooed twice with 0.1 ml of White Rain shampoo, then rinsed with 400 ml of water. Any excess water was squeezed from the tress and the product was applied as detailed in Table I below.

TABLE I

| Product | Treatment Procedure |
|---|---|
| Composition of Example 1 | Apply 0.5 ml product to damp hair, work through hair. Wait 1 minute. Rinse with 200 ml H₂O. |
| Tame | Same as above. |
| Adorn Extra Hold | Roll hair on 0.5 inch diameter curler immediately after shampooing. Dry at 42° C. for 30 minutes and remove curler. Spray hair tress wih product for 5 seconds from a distance of 10 inches. |
| Mink Difference Mousse Regular | Apply 0.4 g product after shampooing. without rinsing. Work through hair. |
| Mink Difference | Apply 0.2 ml product after |

TABLE I-continued

| Product | Treatment Procedure |
|---|---|
| Liquid Stylizer | shampooing, without rinsing. Work through hair. |

Table II gives the % curl retention of the various products.

The tress was then rolled on a 0.5 inch diameter roller and dried in a 42° C. oven for 30 minutes. The tress was allowed to cool to room temperature, and then was placed in a 90% relative humidity chamber at 70° F. (21° C.) for 30 minutes. The curler was then removed, the tress was combed through once, and the length of the curled tress was measured. This length was taken as the initial length, Lo. The curl was again placed in the relative humidity chamber. The length of the curl was measured after one and two hours had elapsed, giving the Lt measurements. Percent curl retention was calculated using the formula below:

$$\% \text{ Curl Retention} = \frac{L - Lt}{L - Lo} \times 100$$

L = length of tress fully extended
Lo = length of hair at time 0
Lt = length of hair at time t The results were as shown in Table II:

TABLE II

| | % Curl Retention at 70° C., 90% Relative Humidity | | | | |
|---|---|---|---|---|---|
| Time Elapsed | Composition of Example 1 | Tame | Adorn Extra Hold | Mink Difference Mousse Regular | Mink Difference Liquid Stylize |
| 1 Hour | 79 | 78 | 64 | 69 | 72 |
| 2 Hours | 69 | 55 | 44 | 62 | 62 |

EXAMPLE 2

The ease of removal of the composition of this invention was demonstrated by the following procedure.

Four five-inch long, 1 g tresses of dark brown, virgin hair were used. Tress A was shampooed twice with 0.1 ml of a conventional shampoo (For Oily Hair Only), then was dried in a 42° C. oven for 20 minutes. This procedure was repeated ten times, after which the silicon content of the hair was determined by analysis to be 170 ppm.

Tress B was shampooed twice with 0.1 ml of the same shampoo, and 0.5 ml of the composition described in Example 1 was applied to and worked through the tress, and allowed to remain for one minute. The tress was then rinsed with 200 ml of water, dried in a 42° C. oven for 20 minutes, and found by analysis to contain 490 ppm silicon.

Tresses C and D were each shampooed twice with 0.1 ml of the same shampoo as above. Each was then subjected to ten successive repetitions of the following sequence of steps: treating with 0.5 ml of the composition of Example 1 for one minute, rinsing with 200 ml water, drying 20 minutes ina 42° C. oven, and shampooing twice with 0.1 ml of the same shampoo as above. Analysis showed the tresses then contained an average of 245 ppm of silicon.

The result with Tress A showed the silicon content of the hair not treated with the composition of Example 1; Tress B showed the silicon content after one treatment and no shampooing; and Tresses C and D showed successive treatments followed by shampooing each time resulted in no substantial buildup of polysiloxane; i.e. that substantially all of the polysiloxane was removed at each shampooing.

EXAMPLE 3

The following example serves to demonstrate the effectiveness of this invention in preventing water loss through human skin.

A composition according to the invention was formed by mixing 7 g Dow Corning Q2-7119 (a carboxylic-acid-functional dimethylsilicone), 3 g of Dow Corning 478 (50% isopropanol and 50% aminomethoxy-functional dimethylsilicone), and 20 ml of diethyl ether. This mixture was slowly added to a solution of 1 g sodium lauryl sulfate in 89 g distilled water. This mixture was subjected to high-shear mixing until a stable white emulsion or dispersion was produced. The ether and isopropanol were removed from the emulsion under reduced pressure on a rotary evaporator. The resultant emulsion was heated at 100° C. for one hour. This stable, milk white emulsion, when spread on skin, dried rapidly to a clear, imperceptible film, dry to the touch and elastic with the skin.

To measure water loss through the skin, a ServoMed Evaporimeter Epl (ServoMed Co., Sweden) was employed. The pretreatment rate of water loss was measured at a marked area on each forearm of four subjects. Two drops of the composition described above were spread on one of the marked sites per subject. The emulsion was allowed to dry and equilibrate for an hour. The rate of water loss at the treated site and untreated site was measured on each subject. The average reduction in the rate of transepidermal water loss at the treated sites was 23.3%, compared to the rate of water loss at the untreated site. This demonstrates the efficacy of the present invention, the reduction in rate of water loss through the skin being almost twice as great as that produced by a conventional commercially available moisturizer under the same conditions.

What is claimed is:

1. A composition comprising a solution in a volatile organic solvent of a mixture comprising two types of polysiloxanes having the following average compositions:

$$\text{A}-\underset{\underset{R}{|}}{\overset{\overset{R}{|}}{\text{SiO}}}-\left[\underset{\underset{R}{|}}{\overset{\overset{R}{|}}{\text{SiO}}}\right]_m\left[\underset{\underset{Q-COOR'}{|}}{\overset{\overset{R}{|}}{\text{SiO}}}\right]_n\underset{\underset{R}{|}}{\overset{\overset{R}{|}}{\text{Si}}}-\text{A} \quad \text{Type I}$$

in which
R is a monovalent hydrocarbon group having 1 to 20 carbon atoms,
R' is hydrogen or a monovalent hydrocarbon group,
Q is a divalent hydrocarbon group having 1 to 8 carbon atoms,
A is either —R or —Q—COOR',
m and n are positive integers, the sum of m and n being from 10 to 300, and
in which at least two —COOH groups are present, $$\text{B}-\underset{\underset{R}{|}}{\overset{\overset{R}{|}}{\text{SiO}}}-\left[\underset{\underset{D}{|}}{\overset{\overset{R}{|}}{\text{SiO}}}\right]_p\left[\underset{\underset{D}{|}}{\overset{\overset{C}{|}}{\text{SiO}}}\right]_q\left[\underset{\underset{T-NHCH_2CH_2NHR''}{|}}{\overset{\overset{R}{|}}{\text{SiO}}}\right]_r\underset{\underset{R}{|}}{\overset{\overset{R}{|}}{\text{Si}}}-\text{B} \quad \text{Type II}$$

in which
R is a monovalent hydrocarbon group having 1 to 20 carbon atoms,
R" is hydrogen or R
B is —R or —OH or —OR or —TNHCH$_2$CH$_2$NHR"
C is —OH or —OR
D is —R, —OH or —OR
T is a divalent hydrocarbon group having 1 to 8 carbon atoms,
p, q and r are positive integers, the sum of p, q and r being from 10 to 300, and r is at least 2,
the molar ratio of Type I to Type II being from 1:4 to 9:1.

2. A composition for application to hair or skin made by dispersing in water a composition as claimed in claim 1 followed by removal of said solvent from said dispersion, the amount of said polysiloxanes being from 0.25 to 30% by weight of the dispersion.

3. A composition as claimed in claim 1 in which R is an alkyl or benzyl group having 1 to 7 carbon atoms, R' is an alkyl group having 1 to 4 carbon atoms, Q is an alkylene group having 1 to 4 carbon atoms, and
in which T is an alkylene group having 1 to 4 carbon atoms.

4. A composition for application to hair or skin made by dispersing in water a composition as claimed in claim 3 followed by removal of said solvent from said dispersion, the amount of said polysiloxanes being from 0.25 to 30% by weight of the dispersion.

5. The method of treating hair to improve its set-retaining characteristics which comprises applying to the hair a composition as claimed in claim 2 with or without subsequent rinsing, forming the hair into the desired configuration and allowing it to dry.

6. The method of treating hair to improve its set-retaining characteristics which comprises applying to the hair a composition as claimed in claim 4 with or without subsequent rinsing, forming the hair into the desired configuration and allowing it to dry.

7. The method of treating human skin to decrease the transepidermal water loss thereof which comprises applying thereto a composition as claimed in claim 2 and allowing it to dry.

8. The method of treating human skin to decrease the transepidermal water loss thereof which comprises applying thereto a composition as claimed in claim 4 and allowing it to dry.

9. The method of making a composition for application to hair or skin which comprises
dissolving in a volatile organic solvent a mixture comprising two types of polysiloxanes having the following average compositions:

$$\text{A}-\underset{\underset{R}{|}}{\overset{\overset{R}{|}}{\text{SiO}}}-\left[\underset{\underset{R}{|}}{\overset{\overset{R}{|}}{\text{SiO}}}\right]_m\left[\underset{\underset{Q-COOR'}{|}}{\overset{\overset{R}{|}}{\text{SiO}}}\right]_n\underset{\underset{R}{|}}{\overset{\overset{R}{|}}{\text{Si}}}-\text{A} \quad \text{Type I}$$

in which R is a monovalent hydrocarbon group having 1 to 20 carbon atoms,

R' is a hydrogen or a monovalent hydrocarbon group,

Q is a divalent hydrocarbon group having 1 to 8 carbon atoms

A is either —R or —Q—COOR', m and n are positive integers, the sum of m and n being from 10 to 300, and in which at least two —COOH groups are present,

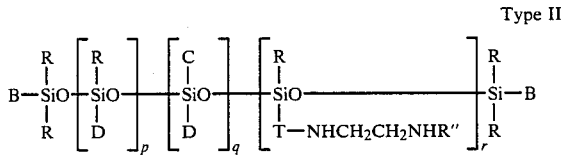
Type II in which R is a monovalent hydrocarbon group having 1 to 20 carbon atoms, R" is hydrogen or R B is —R or —OH or —OR or —TNHCH$_2$CH$_2$NHR"

C is —OH or —OR

D is —R, —OH or —OR

T is a divalent hydrocarbon group having 1 to 8 carbon atoms, p, q and r are positive integers, the sum of p, q and r being from 10 to 300, and r is at least 2, the molar ratio of Type I to Type II being from 1:4 to 9:1, dispersing said solution in water, the amount of said polysiloxanes being from 0.25 to 30% by weight of the dispersion and removing said solvent from said dispersion.

10. The method as claimed in claim 9 in which R is an alkyl or benzyl group having 1 to 7 carbon atoms, R' is an alkyl group having 1 to 4 carbon atoms, Q is an alkylene group having 1 to 4 carbon atoms, and in which T is an alkylene group having 1 to 4 carbon atoms.

11. A composition comprising an aqueous medium having dispersed therein from 0.25 to 30% by weight of a mixture comprising two types of polysiloxanes having the following average compositions:

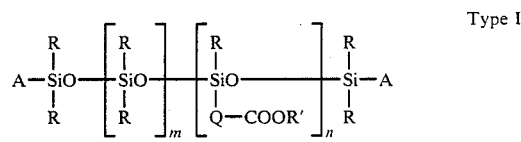
Type I in which

R is a monovalent hydrocarbon group having 1 to 20 carbon atoms,

R' is hydrogen or a monovalent hydrocarbon group,

Q is a divalent hydrocarbon group having 1 to 8 carbon atoms,

A is either —R or —Q—COOR', m and n are positive integers, the sum of m and n being from 10 to 300, and in which at least two —COOH groups are present,

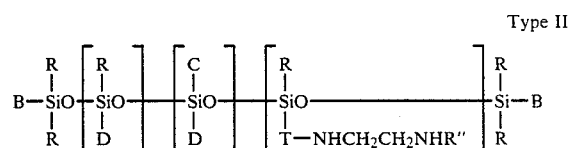
Type II in which R is a monovalent hydrocarbon group having 1 to 20 carbon atoms, R" is hydrogen or R B is —R or —OH or —OR or —TNHCH$_2$CH$_2$NHR"

C is —OH or —OR

D is —R, —OH or —OR

T is a divalent hydrocarbon group having 1 to 8 carbon atoms, p, q and r are positive integers, the sum of p, q and r being from 10 to 300, and r is at least 2, the molar ratio of Type I to Type II being from 1:4 to 9:1, said dispersion being characterized by the fact that when applied to hair or skin and dried it can be essentially completely removed by washing with an aqueous solution of surface active agent at room temperature.

12. The method of treating hair to improve its set-retaining characteristics which comprises applying to the hair a composition as claimed in claim 11 with or without subsequent rinsing, forming the hair into the desired configuration and allowing it to dry.

13. The method of treating human skin to decrease the transepidermal water loss thereof which comprises applying thereto a composition as claimed in claim 11 and allowing it to dry.

* * * * *